United States Patent [19]

Reasner

[11] Patent Number: 4,974,288
[45] Date of Patent: Dec. 4, 1990

[54] DISPOSABLE PROTECTIVE HANDLE AND SHIELD FOR SURGICAL LUMINAIRE

[76] Inventor: Timm Reasner, 9811-9 Owensmouth Ave., Chatsworth, Calif. 91311

[21] Appl. No.: 469,081

[22] Filed: Jan. 23, 1990

[51] Int. Cl.$^5$ .............................................. A47B 95/02
[52] U.S. Cl. .............................. 16/114 R; 16/111 R; 16/DIG. 19; 16/DIG. 24; 362/804
[58] Field of Search ............. 16/110 R, 111 R, 114 R; 206/223; 362/804

[56] References Cited

U.S. PATENT DOCUMENTS

| | | | |
|---|---|---|---|
| 4,559,671 | 12/1985 | Andrews et al. | 16/111 R |
| 4,605,124 | 8/1986 | Sandel et al. | 206/223 |
| 4,844,252 | 7/1989 | Barron et al. | 206/223 |

FOREIGN PATENT DOCUMENTS

89/07900  9/1989  World Int. Prop. O. ........ 16/110 R

*Primary Examiner*—Richard K. Seidel
*Assistant Examiner*—Patty E. Lee
*Attorney, Agent, or Firm*—Edward W. Osann, Jr.

[57] ABSTRACT

A disposable plastic handle and shield in the form of a first embodiment including a unitary injection molded hollow handle with a threaded upper end portion for engagement with a threaded receptacle on the luminaire of a hospital operating room. An integral, generally circular shield is connected to the handle between the threaded upper end portion and a lightly knurled portion of the handle. The shield includes a pair of spaced apart grooves on its underside, one on each side of the handle serving as live hinges and defining a pair of segments capable of being folded down against the knurled handle or upward against the threaded end of the handle to facilitate packaging. A second embodiment has a shield similar to the first embodiment but which is separate from, rather than integral with, the plastic handle. The shield has a central aperture with a thread that engages the thread of the handle and guides the shield down into abutting engagement with a shoulder integral with the handle at the base of the handle thread.

8 Claims, 3 Drawing Sheets

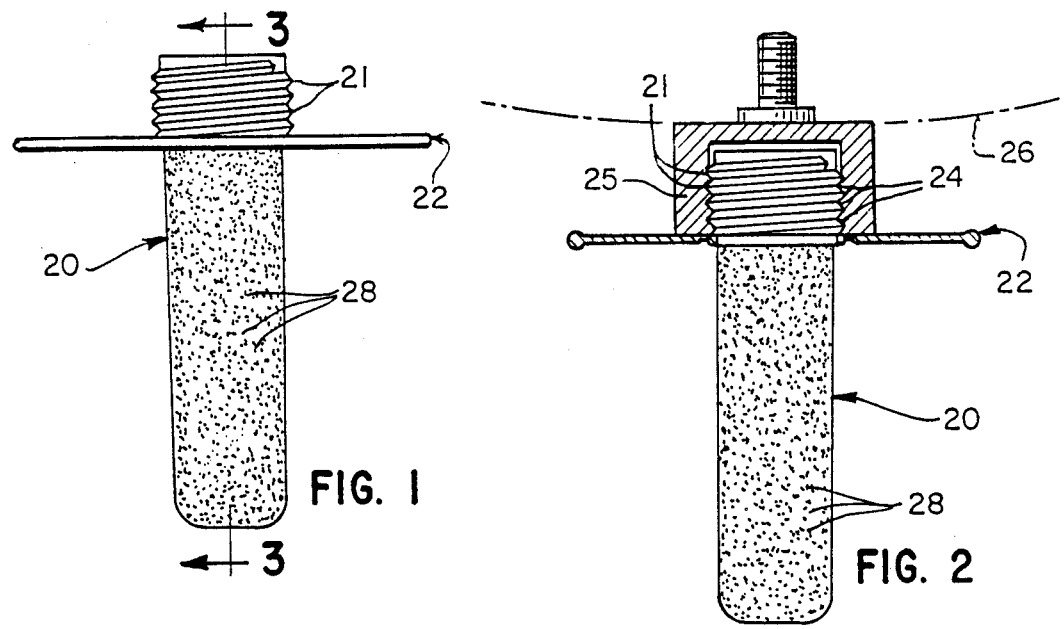
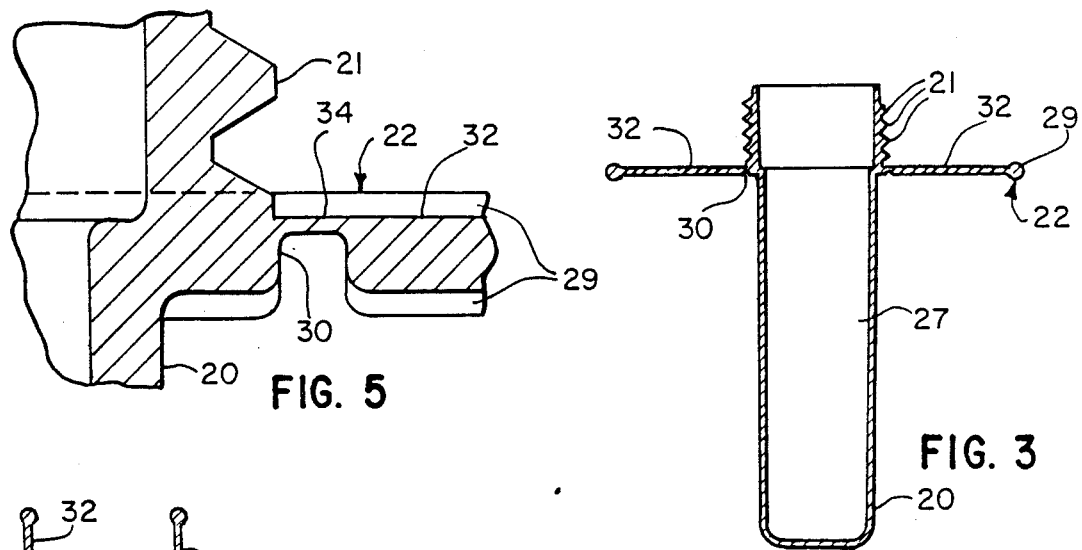
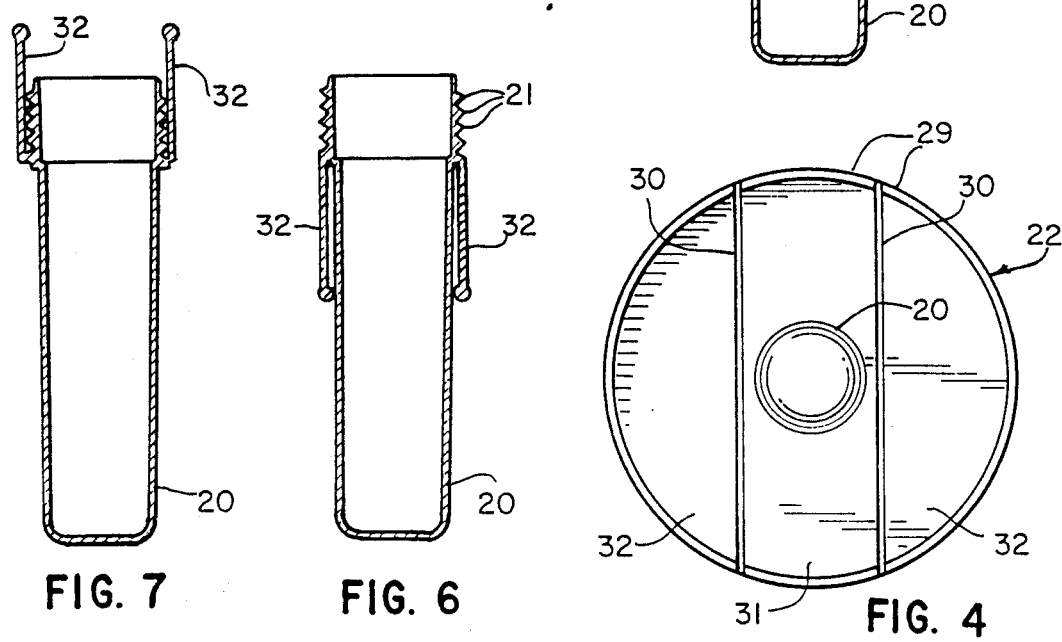

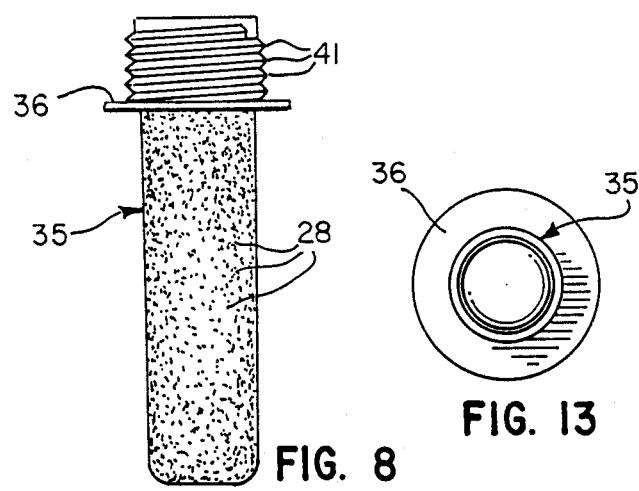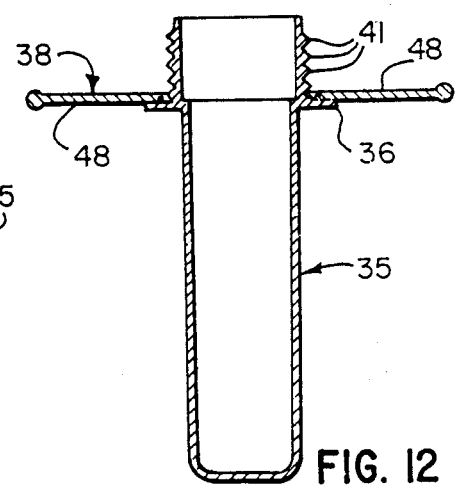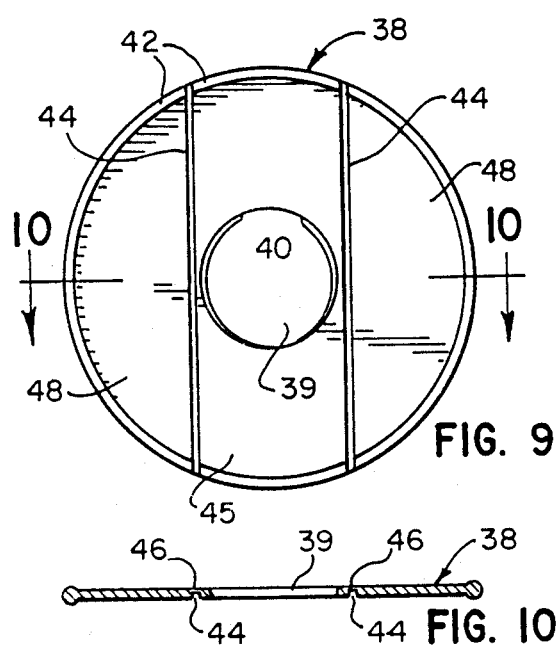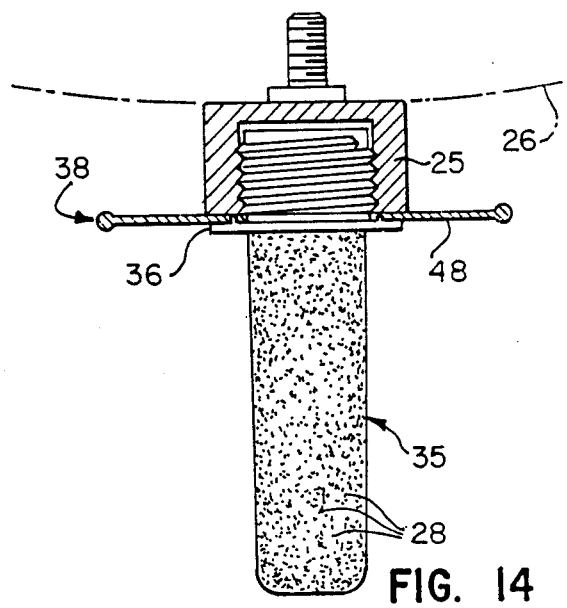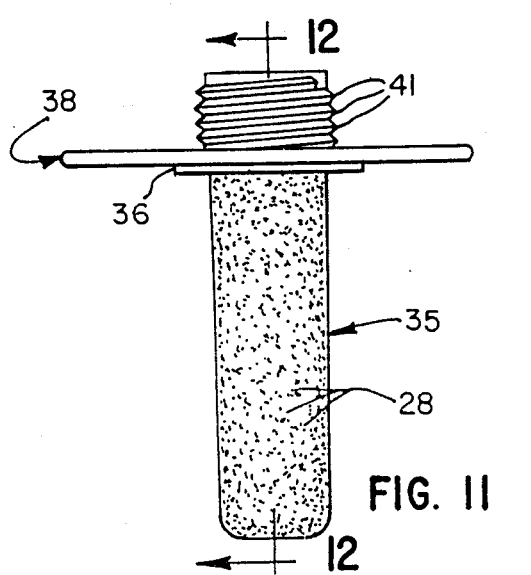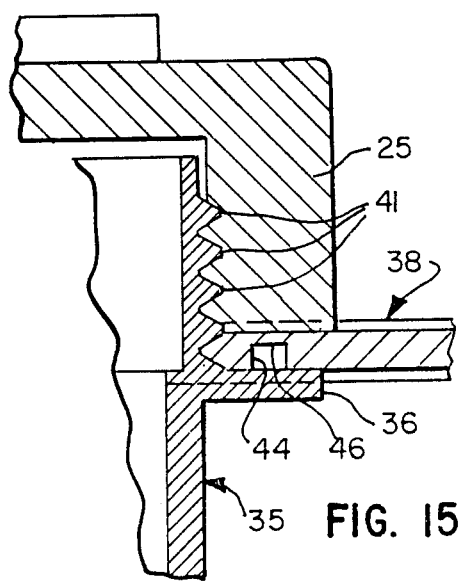

DISPOSABLE PROTECTIVE HANDLE AND SHIELD FOR SURGICAL LUMINAIRE

BACKGROUND OF THE INVENTION

The present invention relates in general to hospital operating room equipment and, more specifically, to the overhead lighting used in a hospital operating room. Such lighting units are constructed in various ways but generally comprise a luminaire with one or more powerful electric lamps housed therein. The luminaire is generally supported from above by means of a balanced suspension which permits both vertical movement as well as angular movement or a combination of the two. This enables the surgeon or the surgical attendant to focus the light on the situs of the operation at the proper angle and with the correct intensity.

In order to permit adjustment of the orientation of the luminaire, a disposable handle is threadedly attached thereto in depending relation from the lower center of the luminaire. The handle in the present instance is formed of sterile plastic with a sterile protective shield of the same material adjacent to its upper end. This enables the operating surgeon or the attendant to reach upward and grip the handle to manipulate the light onto the site of the operation with ease and facility. At the conclusion of the operation, the handle and shield are readily disposed of.

The following prior patents disclose various handles and/or handle covers for use in connection with overhead surgical luminaires:

| U.S. Pat. No. | Patentee | U.S. Pat. No. | Patentee |
| --- | --- | --- | --- |
| 4,559,671 | Andrews et al. | Des 289,206 | Scovill, Jr. et al. |
| 4,605,124 | Sandel et al. | Des. 298,864 | Jefferson |
| 4,844,252 | Barron et al. | | |

SUMMARY OF THE INVENTION

The general object of the present invention is to provide a sterile, disposable handle and shield of light plastic material which threadedly attaches to an operating room luminaire and permits the operating room surgeon or attendant to adjust its orientation manually during the course of an operation.

Another object of the invention is to provide a disposable sterile handle and shield for an operating room luminaire which effectively prevents the surgeon's or attendant's gloved hand from touching anything but the depending handle and shield, thereby avoiding contact with the luminaire itself which is not sterile.

A further object is to provide a sterile handle and shield constituting an inexpensive single use device which is readily detachable from the operating room luminaire upon completion of the operation and may readily be disposed of.

Still another object of the invention is to provide a plastic shield in association with the luminaire handle and which includes a pair of hinged segments coplanar with the central portion of the shield when the handle is installed in the luminaire and which may be folded down or up toward the handle for packaging and shipment.

A further object is to provide a handle and shield of the character set forth above which will be light in weight but have an appropriate margin of strength for its intended use.

The disposable plastic handle and shield referred to above comprises two related embodiments. The first embodiment is a unitary, injection molded piece in the form of a hollow handle with a very lightly knurled finish over the major portion of its body; a threaded upper end portion on the handle for engagement with the threaded socket affixed to the luminaire; an integral, generally circular shield connected to the handle between the threaded upper end and the knurled handle; and a pair of spaced apart grooves in the underside of the shield, one on each side of the handle serving as live hinges and defining a pair of outboard segments, the latter being capable of being folded down against the knurled handle or up against the threaded end of the handle to facilitate packaging of the device.

The second embodiment of the disposable plastic handle and shield is similar to the first embodiment but the shield is separate from rather than integral with the plastic handle. The shield has a narrow thread on the inner periphery of the aperture which engages the threaded portion at the upper end of the handle and screws down to a narrow shoulder at the base of the thread on the handle. This shield also has a pair of grooves on the underside which define narrow hinge areas permitting the outboard segments to be folded down against the handle or up against the threads for packaging as in the case of the first embodiment.

BRIEF DESCRIPTION OF THE DRAWINGS

FIG. 1 is an elevational view of a plastic handle with an integral protective shield adjacent to its upper end and a threaded extension above the shield for engaging the mounting socket of an adapter attached to the overhead surgical lamp.

FIG. 2 is a view similar to FIG. 1 showing the protective shield in cross-section and the threaded extension of the handle engaged in the mounting socket of an adapter attached to the surgical lamp.

FIG. 3 is a vertical sectional view taken axially through the handle and shield of FIG. 1 in the plane of the line 3—3.

FIG. 4 is a bottom view of the protective shield adjacent to the threaded end of the handle shown in FIG. 1.

FIG. 5 is an enlarged fragmentary detail view illustrating one of the grooves on the underside of the protective shield which is integral with the threaded end of the handle.

FIGS. 6 and 7 are vertical sectional views through the handle and shield of FIG. 3, FIG. 6 with the outer wings of the shield folded down and FIG. 7 with the outer wings of the shield folded up.

FIG. 8 is an elevational view of a plastic handle without the protective shield but having a narrow annular shoulder at the upper end portion of the handle supporting the shield.

FIG. 9 is a bottom view of the underside of the protective shield illustrating the thread in the central aperture which engages the thread on the upper-end portion of the handle.

FIG. 10 is a transverse sectional view taken diametrically through the protective shield in the plane of the line 10—10 in FIG. 9.

FIG. 11 is an elevational view of a plastic handle similar to that shown in FIG. 8 but having the protective shield screwed down the threads of the handle to abut solidly against the annular shoulder thereon.

FIG. 12 is a transverse sectional view through the handle of FIG. 11 taken in the plane of the line 12—12 in FIG. 11.

FIG. 13 is a bottom view of the handle of FIG. 8 and showing the annular shoulder at the base of the threaded end.

FIG. 14 is a view of the handle and shield shown in FIG. 14, the shield being shown in section, and the threaded portion of the handle engaging a mounting socket attached to an adapter on the surgical lamp.

FIG. 15 is an enlarged fragmentary detail view taken through the threaded portion of the handle, the annular shoulder, the adjacent portion of the protective shield with the transverse groove therein, and an engaged portion of the mounting socket.

DETAILED DESCRIPTION OF THE INVENTION

Figure 16:
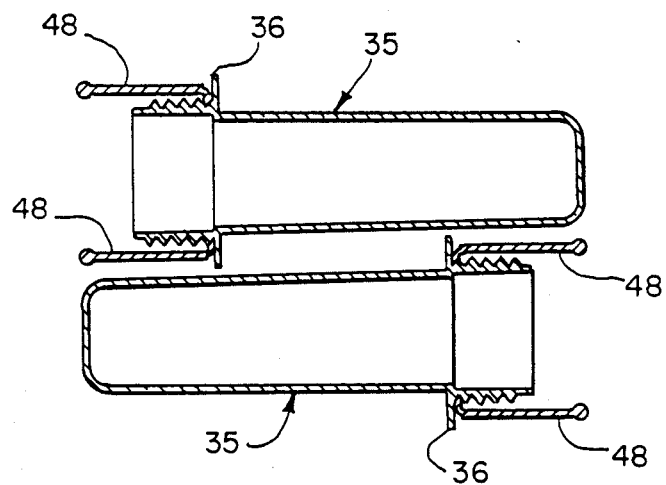
FIG. 16 is a view of the nesting of a pair of handles with the arcuate outer portions of their discs folded upwardly for packaging.

Referring more specifically to FIGS. 1-7, the first embodiment of the invention is there exemplified in a novel disposable handle 20 with threads 21 on its upper end and a circular protective shield 22 interposed between the handle and the threaded end. The latter is adapted to engage the inner threads 24 of socket 25 attached to the adjustable luminaire 26 in the operating room. The handle 20 in the present instance has a hollow interior 27 but is sufficiently strong to enable a surgeon or attendant to engage the handle and adjust the luminaire 26. To facilitate a positive grip on the handle 20, its surface is slightly roughened with small closely-spaced indentations 28.

The protective shield 22 is fashioned as a relatively thin, flat disc surrounded by a small bead 29 of generally circular cross-section with a diameter slightly greater than the thickness of the shield or disc 22. In the present instance, the shield 22 is integrally connected to the handle 20. Formed in the lower face of the shield 22 and spaced relatively close to the threads of the handle 20 are a pair of parallel grooves 30. The grooves 30 divide the shield into a rigid central section 31 and a pair of outboard sections 32 of segmental shape hingedly connected to the central section (FIGS. 3-5).

Referring more specifically to FIGS. 3 and 5, it will be noted that the hinge area of one of the grooves 30 in FIG. 3 has been circled and marked 30a to identify it. This area is depicted in greatly enlarged form in FIG. 5 to show more clearly the area of the groove 30 and the extremely thin, flexible cross-sectional area 34 connecting the segment 32 to the base of the threaded portion of the handle. The area 34 serves as a living hinge which is adapted to flex repeatedly without failure whether the segment is flexed upwardly or downwardly. The area 34 in the opposite groove 30 behaves in an identical manner.

When the handle is screwed into the threaded socket 25 on the luminaire, the wing segments 32 can be pushed up into coplanar condition. The overlapping diameter of the socket 25 will tend to hold the wing segments 32 in that condition and prevent them from being pushed up further. This arrangement prevents the surgeon's gloved hand from accidental contact with the non-sterile luminaire 26.

Turning next to FIGS. 8-15, another embodiment of the invention is disclosed therein. In this instance, the handle 35 is similar to the handle 20 described earlier herein having a slightly roughened surface with small closely spaced indentations 28 (FIGS. 8, 11, 14). The handle 35 differs from the former, however, in that the handle 35 has an integral annular shoulder 36 spaced adjacent the lower end of the threads 41 (FIGS. 8, 11, 12, 13, 14, 15). This embodiment also has a circular shield 38 similar to the one described above and shown in FIGS. 1-7, supra. The shield 38, unlike the shield 22, is separate from the handle but is provided with a large central aperture 39 which includes a narrow inside thread 40 (FIG. 9). The shield 38 may be readily assembled on the handle 35 by screwing it down the handle threads 41 until it bottoms out on the annular shoulder 36.

With the exception of the threaded central aperture 39, the remaining features of the shield 38 conform substantially to those of the shield 22 described above. The shield 38 (FIGS. 9, 10, 15) thus comprises a small diameter bead 42 bordering its periphery. It has a pair of parallel grooves 44 on its underface closely straddling the central aperture 39 and the rigid central section 45 of the shield. Each of the grooves has a thin flexible hinge area 46 (FIGS. 10, 12, 15) delineating a pair of segmental outboard sections 48. With the handle 35 in the condition shown in FIG. 12, the outboard segments may be folded approximately 90 degrees up against the threaded portion 41 of the handle for packaging.

For the purpose of demonstrating the operation of the second embodiment of the present invention, an operating room attendant in sterile garb will remove a sterile shield 38 from its package and thread it onto a sterile handle until it abuts the annular shoulder 36 as illustrated in FIGS. 9, 10, 11 and 12. The handle 35, with shield 38 assembled thereon, is then threaded into the socket fitting 25 of the luminaire until the shield 38 is tightly clamped between the shoulder 36 of the handle and the bottom annular surface of the luminaire socket fitting 25. This arrangement clamps and maintains the shield 38 in relatively rigid horizontal position enabling the operating surgeon to grip the handle 35 and adjust the lighting without violating sterile condition.

Figures 17, 18:
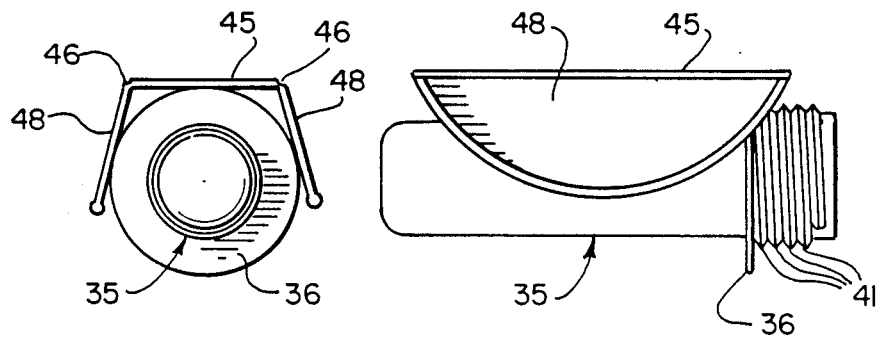
FIGS. 17 and 18 show side and end views, respectively, of a handle and disc folded for packaging. While the present invention is susceptible of various modifications and alternative constructions, there is no intention to limit the invention to the specific form illustrated and described herein. On the contrary, the intention is to cover all modifications and alternative constructions falling within the spirit and scope of the invention as set forth in the appended claims.

Referring next to FIGS. 16-18, various arrangements for packaging handles and shields are there shown. In FIG. 16, two handles 35 are placed side by side in opposite directions with the segmental sections 48 of their shields folded up against the threaded ends of their handles 35. They can then be wrapped with a paper strap or a paper or plastic film enclosure for packaging and shipment.

FIGS. 17 and 18 show another arrangement for packaging a handle 35 and shield 38. In this instance, the shield 38 is placed over the handle 35 with the segmental outboard sections 4–8 folded down into contact with the peripheral edge of the annular shoulder 36. The handle and shield in this condition may then be wrapped for shipment.

I claim as my invention:

1. A disposable, sterile plastic handle for directing an overhead luminaire used in a hospital operating room and comprising, in combination:
   (a) a hollow plastic handle with a threaded upper end portion and a closed lower end;
   (b) means defining a plurality of minute indentations in said handle defining a gripping area;
   (c) a protective circular shield integral with said handle and situated between said gripping area of said handle and said threaded upper end portion of the latter;
   (d) a relatively small diameter peripheral bead bordering said circular shield;
   (e) means defining a pair of laterally spaced parallel grooves in the underside of said shield dividing said shield into a central section integrally connected to said handle and a pair of segmental sections outboard from said central section; and
   (f) said grooves in said shield leaving relatively thin flexible hinge connections between said central section and said segmental sections.

2. The disposable plastic handle and shield of claim 1 wherein said shield is reinforced by a small peripheral bead having a diameter slightly greater than the thickness of said shield.

3. A disposable plastic handle for use on an overhead luminaire in a surgical suite and comprising the combination of:
   (a) a hollow plastic handle with a threaded upper end portion and a closed lower end;
   (b) a protective circular shield integral with said handle and situated adjacent the lower end of said threaded upper end portion;
   (c) means defining a pair of laterally spaced parallel grooves in the underside of said shield dividing same into a central section integral with said handle and a pair of segmental sections outboard from said central section;
   (d) said grooves in said shield defining relatively thin flexible hinge connections between said central section and said segmental sections; and
   (e) each said segmental section being capable of moving through an arc of substantially 180 degrees upwardly or downwardly for packaging.

4. A disposable, sterile plastic handle for use on an overhead luminaire in a surgical suite comprising, in combination:
   (a) a hollow plastic handle with a threaded upper end portion and a closed lower end;
   (b) a shoulder integral with said handle between said threaded upper end portion and the gripping area of said handle;
   (c) a protective circular shield bordered by a small diameter peripheral bead;
   (d) said shield having a relatively large diameter threaded central aperture engaging said shoulder of said handle;
   (e) means defining a pair of laterally spaced parallel grooves in the underside of said shield dividing it into a central section threaded down against said shoulder and a pair of segmental sections outboard from said central section; and
   (f) said grooves in said shield leaving relatively thin flexible hinge connections between said central section and said segmental sections.

5. The combination set forth in claim 4, wherein said handle includes a plurality of minute indentations defining a gripping area thereon.

6. The combination set forth in claim 4, wherein each said segmental section is capable of moving on said flexible hinge connections through an arc of substantially 180 degrees upwardly or downwardly for packaging.

7. The combination set forth in claim 5, wherein said handle with said shield screwed down against said shoulder may be threaded into the socket of a surgical suite luminaire locking all sections of said shield in a rigid coplanar position precluding loss of sterility when the handle is gripped by the surgeon.

8. A disposable, sterile plastic handle for directing an overhead luminaire used in a hospital operating room and comprising, in combination:
   (a) a hollow plastic handle with a threaded upper end portion and a closed lower end;
   (b) means defining a plurality of minute indentations in said handle defining a gripping area;
   (c) a protective circular shield mounted on said handle between said gripping area of said handle and said threaded upper end portion of the latter;
   (d) means defining a pair of laterally spaced parallel grooves in the underside of said shield dividing said shield into a central section integrally connected to said handle and a pair of segmental sections outboard from said central section; and
   (e) said grooves in said shield leaving relatively thin flexible hinge connections between said central section and said segmental sections.

* * * * *